United States Patent [19]

Sutka et al.

[11] Patent Number: 4,678,748
[45] Date of Patent: Jul. 7, 1987

[54] **PROCESS FOR THE PRODUCTION OF IMMUNOBIOLOGICAL PREPARATIONS APPLICABLE IN THE DIAGNOSIS, PREVENTION AND/OR TREATMENT OF *CANDIDA GUILLIERMONDII* INFECTIONS**

[76] Inventors: Pal Sutka; Klara Sutka, both of 60/c Meszaros u., Budapest 1016, Hungary

[21] Appl. No.: 319,711

[22] Filed: Nov. 9, 1981

[51] Int. Cl.$^4$ .................... C12P 21/00; G01N 33/569; C12N 1/16; A61K 39/00
[52] U.S. Cl. ............................................ 435/68; 435/7; 435/255; 435/259; 435/921; 424/85; 424/88
[58] Field of Search ................. 435/7, 29, 34, 68, 921, 435/243, 254, 255, 259; 424/85, 88, 93

[56] References Cited

U.S. PATENT DOCUMENTS

| 2,598,659 | 6/1952 | DeBaer | 424/88 |
| 3,855,063 | 12/1974 | Nagasawa et al. | 435/68 |
| 3,975,517 | 8/1976 | Wilson | 424/93 |

FOREIGN PATENT DOCUMENTS

| 137403 | 9/1979 | German Democratic Rep. | 435/68 |
| 55-68299 | 5/1980 | Japan | 435/34 |
| 1319114 | 6/1973 | United Kingdom | 435/921 |

OTHER PUBLICATIONS

Sutherland, *Handbook of Experimental Immunology*, Third Edition, Blackwell Scientific Publications, London, 2.1, 2.7, 2.8, 2.14–2.17, (1978).
Müller, Med. Microbiol. Immunol., 167: 211–222, (1979).
Greenfield et al, Abstracts Annual Meeting American Society Microbiology, 81: 323, (1981).
Moser et al, Inf. Immun., 27(3), 140–149, (Jan. 1980).
Rogozlin et al, Chemical Abstracts, 82: 56032x, 445, (1975).

*Primary Examiner*—Esther M. Kepplinger
*Attorney, Agent, or Firm*—Keil & Weinkauf

[57] ABSTRACT

The invention relates to a process for the production of new immunobiological preparations for the diagnosis, prophylaxis and/or treatment of *Candida guilliermondii* infections. According to the invention one proceeds as follows:

(a) a *Candida guilliermondii* strain is propagated under aerobic conditions at 24–42° C. on a culture medium containing assimilable carbon and nitrogen sources, the resulting population(s) is (are) maintained under identical conditions for a prolonged period, therafter the fungus cells are separated from the culture, washed, ruptured mechanically, extracted, the extract is treated with a polar organic solvent, and the resulting precipitate is converted into an immunobiological preparation either as such or after further purification, or (b) a *Candida guilliermondii* strain is cultivated for 48–72 hours under aerobic conditions at 24°–42° C. on a culture medium containing assimilable carbon and nitrogen sources, the resulting culture is optionally propagated further to produce two or three new populations, then the fungus cells are separated from the culture, washed, ruptured mechanically, extracted, then, if desired, a polar organic solvent is added to the extract, and the resulting precipitate is converted into an immunobiological preparation either as such or after further purification, or (c) a *Candida guilliermondii* strain is cultivated for 48–72 hours under aerobic conditions at 24°–42° C. on a culture medium containing assimilable carbon and nitrogen sources, then the culture is killed, the killed cells are separated and converted then into an immunobiological preparation either as such or after purification.

6 Claims, No Drawings

PROCESS FOR THE PRODUCTION OF IMMUNOBIOLOGICAL PREPARATIONS APPLICABLE IN THE DIAGNOSIS, PREVENTION AND/OR TREATMENT OF *CANDIDA GUILLIERMONDII* INFECTIONS

The invention relates to a process for the production of new immunobiological preparations applicable in the diagnosis, prevention and/or treatment of *Candida guilliermondii* infections of mammals. The new preparations produced according to the invention can be applied to particular advantage in human therapeutics and veterinary for the diagnosis of *Candida guilliermondii* infections, immunization of subjects exposed to such infections, as well as in the treatment of the disease.

Enzootic candidiasis caused by *Candida guilliermondii* was recognized first on ruminants in 1959 [Hauptman, B. et al.: Med. Vet. 17, 22 (1961)]. Further investigations have revealed that on cattle *Candida guilliermondii* attacks primarily the urogenital tract, and is the causative of several disorders, such as abortion of cows, inflammatory diseases of the urogenital organs (uterus, seminal gland, epididymis, udder, kidney, etc.) and various other reproductive disorders. The occurrence of *Candida guilliermondii* infections, the clinical, pathological and histopathological patterns of the infection, the results of microbiological investigations performed on such fungi and the taxonomic classification of fungus strains isolated from the organisms of infected cattle are described in detail in the following references: Sutka, P. et al.: Magyar Allatorvosok Lapja 33, 151; 155; 837 (1978); Decun, M. et al.: Revta Zootech. Vet. Med. 23, 39 (1973).

Based on the available literature data *Candida guilliermondii* infections appear primarily in ruminants, however, the fungus is pathogenic for humans, too. *Candida guilliermondii* fungi were also detected in human organism in the most diverse clinical pictures, such as infections of the urogenital tract [Harding, S. A. et al.: Clin. Mic. 2, 222 (1975)], ocular infections [Segal et al.: Mycopath. Mycol. Appl. 54, 32 (1974)], endocarditis [Utley, J. R. et al.: Circulation 48, 42 (1973)], as well as systemic candidiases [Kozinn, P. J. et al.: Sab. 7, 98 (1969)].

In human therapy systemic candidiases, mainly those caused by *Candida albicans*, are diagnosed primarily by methods applicable for the laboratory detection of humoral antigens, such as agglutination, latex agglutination, indirect fluorescence, immunodiffusion, counterimmunoelectrophoresis, etc. [Taschdjian, C. L. et al.: Amer. J. Clin. Pathol. 57, 195 (1972)]. These diagnostic methods require a well-trained staff with a skill exceeding the average. Up to now no specific *Candida guilliermondii* antigen was known which would enable one to diagnose the infection just on the instant in a routine veterinary screening test or even at the bedside of the patient. The invention relates to the preparation of antigens applicable for this purpose.

Taking into account that ruminants, primarily cattle which are of major importance in food industry, suffer serious urogenital and reproductive disorders and disturbances in lactation upon *Candida guilliermondii* infection, which involves substantial economic losses and serious problems in public health, there is a significant need for veterinary preparations for the diagnosis, prophylaxis and treatment of such infections. With respect to the human pathogenic nature of the fungus, appropriate presentation forms of these preparations can also be applied in human therapy. The invention relates to a process for producing such preparations.

The majority of Candida antigens were produced from cells obtained after a 48-72 hours' cultivation of the Candida strain. Up to now little attention was paid to the changes occurring in and the substances produced by Candida cells upon prolonged cultivation. The infected organism contains, however, products of elder Candida cells, too. It has been recognized first by us that new substances are formed in Candida cells upon prolonged cultivation, which can be applied as an instant diagnostic to provoke early hypersensitivity reaction and in the tube precipitation diagnostic technique, furthermore for the immunobiological treatment of the infected organism. Utilizing these substances, *Candida guilliermondii* infections can be diagnosed quickly, even at the bedside of the patient or at the farm, by early hypersensitivity reaction or by serum tube precipitation.

Immunobiological preparations for the diagnosis, prophylaxis and/or treatment of *Candida guilliermondii* infections are prepared according to the invention as follows:

(a) a *Candida guilliermondii* strain is propagated under aerobic conditions at 24°–42° C. on a culture medium containing assimilable carbon and nitrogen sources, the resulting population(s) is(are) maintained under identical conditions for a prolonged period, thereafter the fungus cells are separated from the culture, washed, ruptured mechanically, extracted, the extract is treated with a polar organic solvent, and the resulting precipitate is converted into an immunobiological preparation either as such or after further purification, or (b) a *Candida guilliermondii* strain is cultivated for 48-72 hours under aerobic conditions at 24°–42° C. on a culture medium containing assimilable carbon and nitrogen sources, the resulting culture is optionally propagated further to produce two or three new populations, then the fungus cells are separated from the culture, washed, ruptured mechanically, extracted, then, if desired, a polar organic solvent is added to the extract, and the resulting precipitate is converted into an immunobiological preparation either as such or after further purification, or (c) a *Candida guilliermondii* strain is cultivated for 48-72 hours under aerobic conditions at 24°–42° C. on a culture medium containing assimilable carbon and nitrogen sources, then the culture is killed, the killed cells are separated and converted then into an immunobiological preparation either as such or after purification.

Cultivation of the *Candida guilliermondii* strains is performed preferably at 32°–38° C.

A preferred agent for washing the separated cells is physiological saline solution.

The separated cells can be ruptured on apparatuses conventionally applied for this purpose, e.g. on an X-press apparatus, or cell rupture can be performed by ultrasonic irradiation. The resulting mass is extracted preferably with physiological saline solution.

The extract obtained according to process variant (a) or (b) is treated preferably with a $C_{1-4}$ alcohol, particularly with ethanol.

The precipitate obtained according to process variant (a) or (b) can be purified, if desired, by methods well known in the purification of proteins, such as chromatography, ultrafiltration, dialysis, electrophoresis, methods applying filtration aids and/or detergents, etc.

The immunobiological preparations produced by methods (a), (b) and (c) of the invention are termed in the following as preparations Cg1, Cg2 and Cg3, respectively.

Preparation Cg1 is a protein-containing cell extract isolated from *Candida guilliermondii* cells subjected to a prolonged cultivation. The most important constituents of this cell extract are the toxins of *Candida guilliermondii*Preparation Cg1 can be applied primarily for the diagnosis of *Candida guilliermondii* infections by provoking an early hypersensitivity reaction upon intradermal introduction, and it can also be used for the detection of circulating antibodies by the Durham-tube or capillary tube precipitation method. Moreover, when introduced into the living organism, preparation Cg1 initiates the production of antibodies capable of terminating an already established *Candida guilliermondii* infection.

Preparation Cg2, separated from *Candida guilliermondii* cells subjected to short cultivation, contains much more proteins than preparation Cg1, whereas its toxin content is low. This preparation can be applied primarily in the immunization of living organisms exposed to the risk of infection. Preparation Cg2 can also be used as a diagnostic agent to provoke late hypersensitivity reaction upon intradermal introduction, furthermore it can be applied as an antigen for the diagnosis of the infection in latex agglutination, immunodiffusion and counter-immunoelectrophoresis methods.

Preparation Cg3 consists of killed whole cells of *Candida guilliermondii*, and can be applied primarily for the diagnosis of the early stage of *Candida guilliermondii* infections in laboratory tests (such as agglutination, indirect fluorescence tests, etc.), furthermore to produce stained antigens applicable in ABR (Abortus-Bang-Ring) tests (Hutyra, F. et al.: Spezielle Pathologie und Therapie der Haustiere, VEB Gustav Fischer Verlag, Jena, 1959).

*Candida gulliermondii* strains separated from infected organisms can be applied to great advantage as microorganisms for the production of the above three types of immunobiological preparations. However, known international standard *Candida guilliermondii* strains, such as a strain deposited in Central-bureau voor Schimmelcultures (Delft, Holland) under No. CBS-566, as well as the *Candida guilliermondii* strains deposited in American Type Culture Collection, can also be applied in the process according to the invention.

It is preferred to apply a pre-culture, obtained by cultivating a *Candida gulliermondii* strain for 48–72 hours under aerobic conditions at 24°–42° C. on a culture medium containing assimilable carbon and nitrogen sources, as starting substance for the production of the immunobiological preparations. The following substances can be applied as carbon sources in both the pre-cultivation and the subsequent cultivation steps: glucose, sucrose, maltose, cellobiose, melibiose, melecytose, inulin, arbutin, galactose, sorbose, trehalose, ribose, xylose, L-arabinose, D-arabinose, glycerol, ribitol, D-mannitol, D-dulcitol, L-methyl-D-glycoside, salicin, tartaric acid, citric acid and related compounds. The culture media utilized in the pre-cultivation and subsequent cultivation steps may contain as assimilable nitrogen source e.g. sera, proteose peptone (Difco certified, Difco Laboratories, Detroit, Mich., USA) and other proteoses, substances containing peptone and/or amino acids, etc.

Preparations Cg1 and Cg2 are produced preferably as follows: At the end of the cultivation period the broth is checked for the presence of bacteria, and the fungus cells are separated then from the bacterium-free fermentation broth preferably by centrifuging. The separated cells are washed with water or an aqueous salt solution, preferably physiological saline solution, and subjected then to mechanical rupture. One can proceed e.g. so that the cell precipitate is dried, ground in a sterile mill, the ground substance is sampled periodically, and the grade of rupture is monitored by microscopic examination. Thereafter the ruptured cells are extracted with physiological saline solution. According to another method the separated *Candida guilliermondii* cells are admixed with water or an aqueous salt solution, preferably physiological saline solution, and the resulting suspension is subjected to ultrasonic irradiation. The suspension is sampled at regular intervals, and the grade or rupture is monitored by microscopic examination. In this instance mechanical rupture proceeds simultaneously with the extraction of the ruptured cells. Thereafter the solids (i.e. the broken cell substance) are separated by centrifuging, the supernatant is filtered, and a polar organic solvent, preferably ethanol, is added to the filtrate. If desired, the resulting precipitate can be purified by any of the known methods applied in the purification of proteins (e.g. chromatography, ultrafiltration, dialysis, electrophoresis, etc.). If the immunobiological preparation is to be applied for diagnosis, it is not absolutely necessary to purify the precipitate. As mentioned above, the extract of the ruptured cells obtained in method (b) can also be applied directly for diagnostic purposes. Thus the term "immunobiological preparation", whenever used in connection with preparation Cg2, also extends to such extracts. Otherwise the resulting precipitate is converted into immunobiological preparations by methods well known in the art, utilizing conventional diluents (e.g. physiological saline solution, etc.) and conventional techniques (e.g. dissolution, freezing, freeze-drying, etc.).

Preparation Cg3 is produced according to the invention preferably as follows: At the end of the fermentation stage the *Candida guilliermondii* cells are killed with a cytotoxic agent, such as formaldehyde. One can proceed e.g. so that an aqueous formaldehyde solution is added to the culture in an amount sufficient to adjust the formaldehyde content of the broth to 0.5%, and the broth is incubated then for 6 hours at 37° C. The killed cells can be purified by washing them preferably with physiological saline. Thereafter the killed cells are converted into immunobiological preparations for laboratory diagnostics by methods known per se (e.g. suspending in aqueous medium, freezing, etc.).

Preparations Cg1, Cg2 and Cg3, presented e.g. as powders distributed into ampoulles, can be utilized in the diagnosis of *Candida guilliermondii* infections of living organisms as follows:

Preparations Cg1 and Cg2 can be applied under both in vivo and in vitro conditions, whereas preparation Cg3 can be utilized only for in vitro examinations.

When living organisms are tested for *Candida guilliermondii* infection under in vivo conditions, preparation Cg1 or Cg2 is administered to the test subject as an intradermal injection. When preparation Cg1 is applied, the presence or absence of infection is determined on the basis of early hypersensitivity reaction provoked by the preparation, which is evaluated 1 to 12 hours after injection. A well-separating, growing intumescence appears on the infected subjects at the site of injection, which can no more be observed 24 hours after challenge. When preparation Cg2 is applied, the presence or absence of *Candida guilliermondii* infection is determined on the basis of the tuberculin-type late hypersensitivity reaction, which can be evaluated 36–48 hours after challenge.

Preparations Cg1, Cg2 and Cg3 can be utilized for diagnostic tests performed under in vitro conditions as follows:

The basis of detection is always a precipitate-forming immunobiologcal reaction, wherein negative serum, serum with high precipitin content and serum with agglutinin content are applied as reactants. The preparation of sera with high agglutinin or precipitin content are also included within the scope claimed.

"Negative serum" is the serum obtained from cattle or laboratory animals which give a negative reaction upon testing them with preparation Cg1, Cg2 or Cg3.

Serum with high agglutinin content is prepared so that rabbits are immunized with preparation Cg2 or Cg3 in a standard procedure, thereafter the animals are bleeded, and the serum is separated from their blood in a manner known per se.

Serum with high precipitin content is prepared so that rabbits are immunized with preparation Cg1 in a standard procedure, thereafter the animals are bled, and the serum is separated from their blood in a manner known per se. Serum with high precipitin content can also be obtained from the blood of cattle infected under natural conditions. The serum of such animals is examined with Cg1 allergen e.g. by the Durham-tube or capillary-tube method, then the animals with sera of high precipitin factor are bleeded, and the serum is separated from the blood in a manner known per se.

The following laboratory examinations can be performed with preparations Cg1, Cg2 and Cg3, making use the reagents mentioned above:

1. Durham-tube or capillary-tube precipitation test performed with preparation Cg1:

Negative serum is filled with a pipette into a Durham tube so that no air blow is on the surface of the serum. The tube is filled up to about the half of its volume. Serum with high precipitin content is filled similarly into another Durham-tube, and the serum to be tested is filled into two Durham-tubes. Preparation Cg1 is used in this test as a solution formed with physiological saline. The solution of the immunobiological preparation is layered cautiously into three of the serum samples (negative serum, serum with high precipitin content and one of the serum samples to be examined), whereas the remaining serum sample to be tested is treated with physiological saline solution. The tubes are maintained at room temperature for one hour and then at +5° C. for 24 hours. The boundaries of the two phases are examined visually after 10–15 minutes, 1 hour and 25 hours of standing, and the observations are recorded. If the test serum contains antibodies for *Candida guilliermondii* antigen (preparation Cg1), a precipitation ring appears at the boundary of the two phases.

2. Preparation Cg2 can be applied as antigen in immunodiffusion, latex agglutination and counter-immunoelectrophoresis tests. These tests are performed by methods well known in the art (see e.g. Palmer, D. F. et al.: Serodiagnosis of mycotic diseases, Charles C. Thomas, Ill., USA, 1977).

3. Preparation Cg3 can be applied as antigen in the agglutination and indirect fluorescence methods (see e.g. Palmer, D. F. et al.: Serodiagnosis of mycotic diseases, Charles C. Thomas, Ill., USA, 1977), as well as for the preparation of stained antigens usable in ABR tests (see e.g. Hutyra, F. et al.: Spezielle Pathologie und Therapie der Haustiere, VEB Gustav Fischer Verlag, Jena, 1959).

Preparation Cg2 can also be applied for the preventive immunization of humans and animals exposed to the risk of *Candida guilliermondii* infection. Preparation Cg2 is presented for this purpose in the form of vaccines. These vaccines may contain, beside the active agent and the diluent, a carrier (such as aluminium hydroxide gel) as well, which ensures the slow, gradual release of the active agent. The vaccine can be introduced into the organism to be treated as an intradermal, intramuscular or subcutaneous injection. According to a preferred method of immunization the subjects are vaccinated once again, two weeks after the first one, so that a greater amount of antigen is administerd to the organism with this second vaccination than with the first one. The dose required for immunization depends on numerous factors, such as on the age and general health conditions of the patient, age and breed of the animal, previous immunization treatments, degree of endangeredness, etc.

Preparation Cg1 can also be used in the treatment of humans and animals suffering from *Candida guilliermondii* infection. In such instances the subject to be treated is desensitized first with the preparation, and preparation Cg1 is administered then as an intradermal, intramuscular or subcutaneous injection. Preparations utilized for this purpose may also contain a carrier, such as aluminium hydroxide gel, which ensures the slow, gradual release of the active agent. The treatment is repeated every two weeks so that the amount of antigen administered to the organism is continuously increased from treatment to treatment. The dose required for the treatment depends on numerous factors, such as on the age of the patient, the extent and severity of the disease, the breed of the animal, the method and frequency of treatments, etc.

The invention is elucidated in detail by the aid of the following non-limiting Examples.

EXAMPLE 1

Production of immunobiological preparation Cg1

250 ml of a standard liquid dextrose/peptone/yeast culture medium [see Palmer, D. F. et al.: Serodiagnosis of mycotic diseases, p. 49 (Charles C. Thomas, Ill., USA, 1977)] are filled into a flask of 500 ml capacity. The culture medium is inoculated with a maintained culture of *Candida guilliermondii*, and then incubated for 48 hours at 37° C. under shaking at a rate of 130 r.p.m. The resulting culture is used as inoculum in the subsequent step.

10 liters of the above culture medium are filled into a laboratory fermenter, 20 liters in capacity, and the medium is incoulated with the above culture. Cultivation is performed at 37° C. under aeration and stirring. After 72 hours of cultivation the propagation of the fungus decreases continuously, and finally stops. Cultivation is continued for additional 15 days under the same conditions (prolonged cultivation). Thereafter a sample is taken from the culture for Gram-staining. If the sample gets stained, referring to the presence of bacterial contaminations, the culture cannot be used for the production of immunobiological preparations. The culture, free of bacterial contaminations, is processed as follows: The contents of the fermenter is filled into a centrifuge, and the cells are separated from the liquid by centrifuging for 10 minutes at a rate of 1000 r.p.m. The resulting cell substance is washed three times with physiological saline solution, centrifuged again for 10 minutes at a rate of 1000 r.p.m., then suspended in physiological saline solution, and the suspended cells are ruptured in an X-press type apparatus under a pressure of about 10,000 kg/cm². The solids are separated by centrifuging (30 minutes, 3000 r.p.m.), the supernatant is filtered through a Seitz filter insert, and 4 parts by volume of ethanol are added to the filtrate. The separated precipitate is filtered off, disolved in physiological saline solution, and the solution is freeze-dried at −20° C. Depending on the conditions of fermentation and rupture, about 500 mg of a powdery substance are obtained. This product is filled into ampoulles, and utilized as an allergen in intradermal tests based on early hypersensitivity reactions.

EXAMPLE 2

Production of immunobiological preparation Cg2

250 ml of a standard liquid dextrose/peptone/yeast culture medium are filled into a flask of 500 ml capacity. The culture medium is inoculated with a maintained culture of *Candida guilliermondii*, and then incubated for 48 hours at 37° C. under shaking at a rate of 130 r.p.m. The resulting culture is used as inoculum in the subsequent step.

10 liters of the above culture medium are filled into a laboratory fermenter, 20 liters in capacity, and the medium is inoculated with the above culture. Cultivation is performed at 37° C. for 72 hours under aeration and stirring. Thereafter a 30–40% aqueous formaldehyde solution is added to the culture in an amount to obtain a final formaldehyde concentration of 0.5%, and incubation is continued at 37° C. for 6 hours. A sample is taken from the culture, and the viability of the fungus is checked by inoculating it onto a Sabouraud-dextrose agar plate and incubating the plate at 37° C. for 48 hours. Another sample is taken from the culture for Gram staining. If the sample gets stained, referring to the presence of bacterial contaminations, the culture cannot be used for the production of immunobiological preparations. The culture, free of bacterial contaminations, is processed as follows: The contents of the fermenter is filled into a centrifuge, and the solids are separated from the broth by centrifuging for 10 minutes at a rate of 1000 r.p.m. the solids are separated, washed three times with a 0.85% aqueous sodium chloride solution, and the cells are centrifuged again for 10 minutes at a rate of 1000 r.p.m. The solids are suspended then in a 0.85% aqueous sodium chloride solution, and the cells are ruptured in an X-press type apparatus under a pressure of about 10,000 kg/cm². The resulting cell homogenizate is centrifuged for 30 minutes at a rate of 3000 r.p.m., the supernatant is separated, filtered through a Seitz filter insert, and 4 parts by volume of ethanol are added to the filtrate. The separated precipitate is filtered off, dissolved in physiological saline solution, and the solution is freeze-dried at −20° C. Depending on the conditions of fermentation and cell rupture, about 1500 mg of a powdery substance are obtained. This product is distributed into ampoulles, and utilized as an allergen in intradermal tests based on late hypersensitivity reactions, furthermore as an antigen in latex agglutination, immunodiffusion and counter-immunoelectrophoresis tests.

EXAMPLE 3

Production of immunobiological preparation Cg3

A Sabouraud dextrose-agar slant is inoculated with a maintained culture of *Candida guilliermondii*, and then incubated for 48 hours at 37° C. The fungus developed on the slant culture is suspended in a dextrose/peptone/yeast broth, and the resulting suspension is used as inoculum in the next step.

250 ml of a liquid dextrose/peptone/yeast culture medium are filled into a conic flask, 500 ml in capacity, and the above inoculum is added to the medium. The resulting mixture is incubated at 37° C. for 48 hours under shaking it at a rate of 130 r.p.m. Thereafter a 30–40% aqueous formaldehyde solution is added to the culture in an amount to obtain a final formaldehyde concentration of 0.5%. The flask is mounted again onto the shaker and shaken at a rate of 130 r.p.m. for 6 hours at 37° C. A sample is taken from the resulting culture, and the viability of the fungus is checked by inoculating it onto Sabouraud dextrose-agar plates and incubating the plates at 37° C. for 48 hours. Another sample is taken from the culture for Gram staining. If the sample gets stained, referring to the presence of bacterial contaminations, the culture cannot be used for the production of immunobiological preparations. The culture, free of bacterial contaminations, is processed as follows: The culture is centrifuged for 10 minutes at a rate of 1000 r.p.m., the solid phase, consisting of whole cells, is separated, washed three times with sterile physiological saline solution, and then centrifuged again for 10 minutes at a rate of 1000 r.p.m. A wet cell mass, weighing about 2.5 g, is obtained.

One part by volume of the resulting wet cell mass is suspended in 3 parts by volume of physiological saline solution, a commercially available Merthiolate solution (sodium ethylmercuricthiosalicylate) is added to the suspension in an amount to attain a final concentration of 1:10,000, and the cell suspension is stored at +4° C. This immunobiological preparation can be applied in the laboratory diagnostics for tube agglutination and indirect fluorescence tests, furthermore for the production of stained antigens usable in ABR tests.

The immunobiological preparations produced according to the invention enable one to diagnostize *Candida guilliermondii* infections, and make possible a regular preventive screening and immunization of cattle exposed to such diseases. This involved significant advantages primarily in cattle breeding, since losses due to *Candida guilliermondii* infections can be reduced substantially. Taking into account that humans are also susceptible to *Candida guilliermondii* infections, the diagnostical screenings are of great importance with respect to public health. Moreover, some of the immunobiological preparations produced according to the invention can be applied effectively in the treatment of *Candida guilliermondii* infections, which could not be treated before with immunobiological methods.

What we claim is:

1. A process for producing immunobiological preparations for the diagnosis, prophylaxis and/or treatment of *Candida guilliermondii* infections comprising the steps of:
    a. cultivating a *Candida guilliermondii* strain for 48–72 hours under aerobic conditions at 24°–42° C.

on a culture medium containing assimilable carbon and nitrogen sources;

b. maintaining the resulting populations under aerobic conditions at 24°–42° C. for further cultivation of about 15 days until they are bacterium-free and contain toxins of *Candida guilliermondii;* c. separating, washing, and mechanically rupturing the bacterium-free culture;

d. separating and treating the resulting extract with a polar organic solvent; and e. converting the resulting precipitate into an immunobiological preparation.

2. The process set forth in claim 1 wherein the *Candida guilliermondii* strain is cultivated at 32°–38° C.

3. The process set forth in claim 1 wherein a $C_{1-4}$ alcohol is used as the polar organic solvent.

4. The process set forth in claim 3 wherein ethanol is used as the polar organic solvent.

5. The process set forth in claim 1 for producing an immunobiological preparation in a form applicable in human therapy or veterinary therapy wherein step (e) comprises dissolving the resulting precipitate in a physiologically compatible solvent for human or veterinary therapy.

6. The process set forth in claim 1 wherein the immunobiological preparation produced is presented in the form of an allergen, a soluble antigen or a vaccine.

* * * * *